United States Patent [19]

Nakatani et al.

[11] Patent Number: 4,732,738
[45] Date of Patent: Mar. 22, 1988

[54] COMBUSTIBLE GAS DETECTING ELEMENT

[75] Inventors: Yoshihiko Nakatani, Osaka; Masayuki Sakai, Minamikawachi, both of Japan

[73] Assignee: Matsushita Electric Industrial Co., Ltd., Osaka, Japan

[21] Appl. No.: 496,492

[22] Filed: May 17, 1983

[30] Foreign Application Priority Data

May 17, 1982 [JP] Japan .................................. 57-83443
Aug. 19, 1982 [JP] Japan .................................. 57-144512
Sep. 27, 1982 [JP] Japan .................................. 57-168768

[51] Int. Cl.⁴ ............................................. G01N 27/12
[52] U.S. Cl. ...................................... 422/94; 73/27 R; 338/34; 422/98
[58] Field of Search ..................... 422/94, 95, 97, 98; 73/23, 27 R; 338/34; 324/71.5

[56] References Cited

U.S. PATENT DOCUMENTS 4,045,178  8/1977  Okinaka et al. .................. 73/23 X
4,359,709 11/1982  Nakatani et al. ..................... 422/94

FOREIGN PATENT DOCUMENTS 5480    11/1979  Fed. Rep. of Germany .
2287697  5/1976  France .
2331016  6/1977  France .
2417765  9/1979  France .
0139795 10/1979  Japan .................................. 422/98
22369    1/1981  United Kingdom .
30112    6/1981  United Kingdom .

Primary Examiner—Barry S. Richman
Assistant Examiner—Michael S. Gzybowski
Attorney, Agent, or Firm—Wenderoth, Lind & Ponack

[57] ABSTRACT

Combustible gas detecting element for detecting the existence of combustible gas such as methane, ethane, propane iso-butane and hydrogen. The element comprises $\alpha\text{-}Fe_2O_3$ containing a small amount of sulfate ion ($SO_4^{--}$). By using a precipitation process with urea as a precipitant for preparing the above $\alpha\text{-}Fe_2O_3$, remarkably high stability and reliability can be released. Addition of quadrivalent metal of Sn, Zr or Ti to the $\alpha\text{-}Fe_2O_3$ greatly enhances the gas sensitivity to those gases. Furthermore the sensitivity to carbon monoxide was also enhanced by adding cadmium (Cd) and/or gold (Au).

10 Claims, 11 Drawing Figures

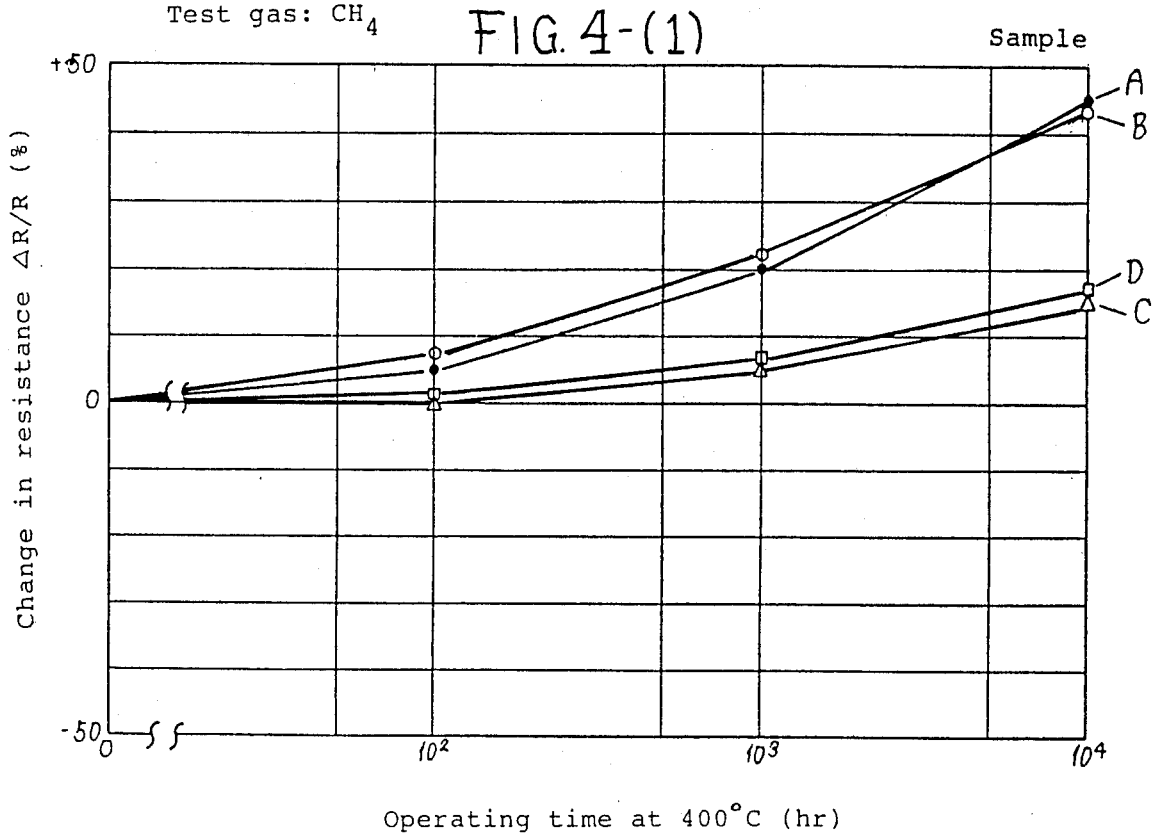
FIG. 4-(1)
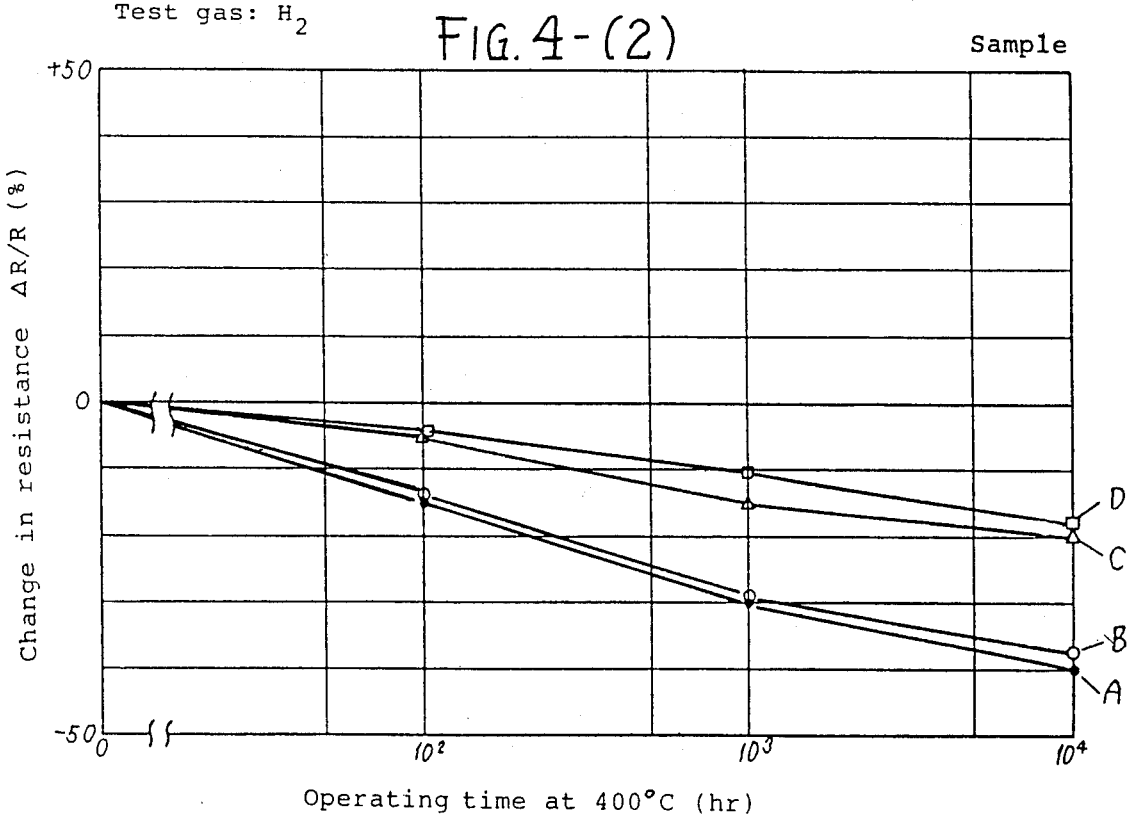
FIG. 4-(2)

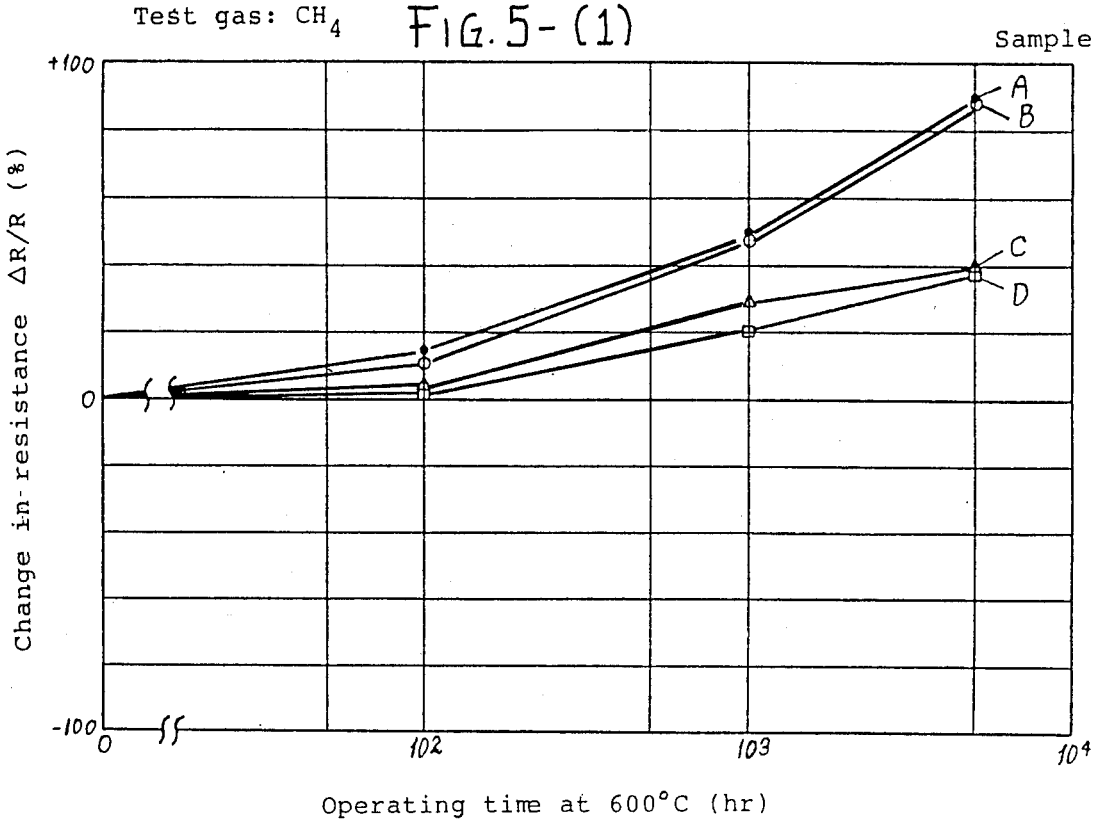
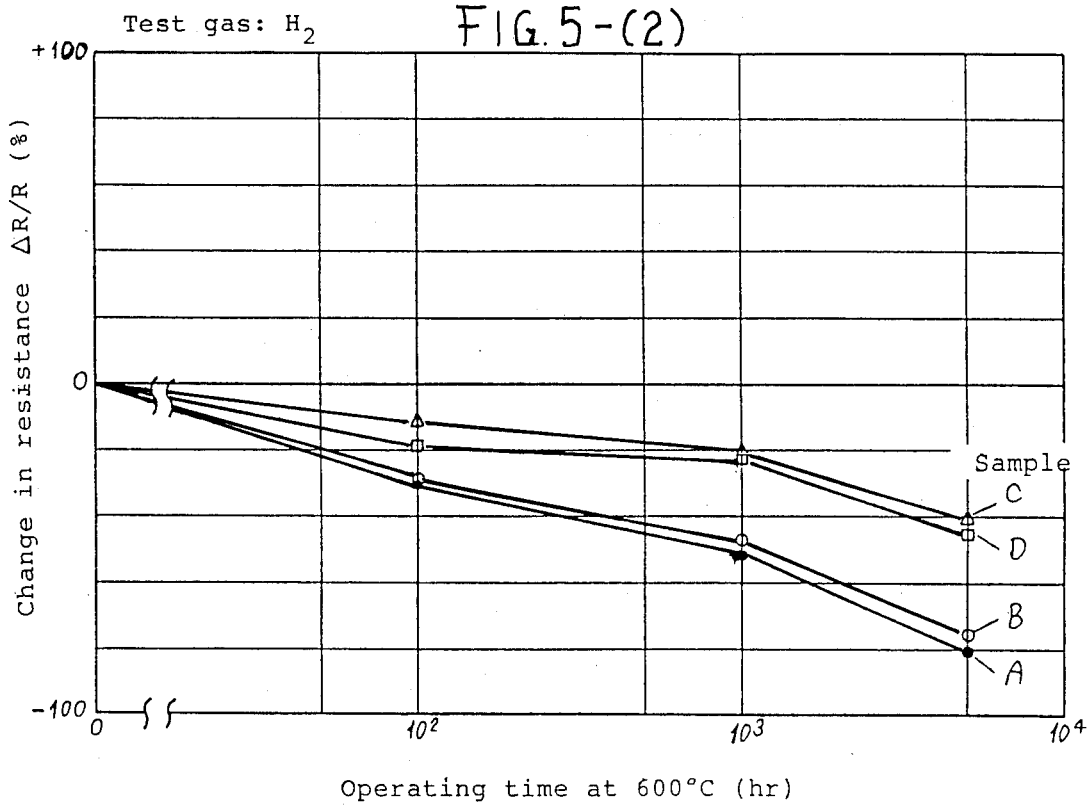

COMBUSTIBLE GAS DETECTING ELEMENT

BACKGROUND OF THE INVENTION

1. Field of the Invention

This invention relates to a combustible gas detecting element which changes its electrical resistance when in contact with a combustible gas, and also relates to a fabrication process for the preparation of the raw material of the detecting element.

2. Description of the Prior Art

As a rule, the methods for detecting a combustible gas by solid materials include two methods, one of which involves detecting a combustible gas by the temperature rise owing to its combustion on a catalyst by means of a resistor such as platinum wire, of which electric resistance is dependent upon the temperature. The other method involves detecting a combustible gas by determining the change in the electrical resistance of a semiconductor accompanied by the adsorption of gas thereon. The former gives an output in proportion to the concentration of gas and accordingly may be used principally for a gas concentration meter and the like. The latter can provide an inexpensive detecting means and accordingly may be used as a gas leak detector and the like.

The present invention provides a gas detecting element of semiconductor type for a combustable gas detecting means according to the latter method.

A gas responsive element is held in an atmosphere of high temperature because a gas detecting element of the semiconductor type requires, in general, a high-speed response. Thus the oxides which are stable in an oxidizing atmosphere are selected as gas responsive elements.

Recently considerable research and development on the materials for a combustible gas detecting element has been conducted, centered on metal oxide semiconductors. This is caused by the problem that explosions due to combustible gas and poisoning due to a noxious gas, like carbon monoxide, are frequently generated in the home and in a variety of factories.

Liquefied natural gas (LNG) containing methane gas as its principal component has come into wide use in homes in many countries. Thus, a gas detecting element for selectively detecting methane gas, which is the principal component of LNG, is also in remarkably great demand.

Of course, a gas detecting element for responding to methane gas has already been developed. However, such gas detecting elements have a variety of defects such as catalyst poisoning due to a variety of gases, low selectivity for methane gas, great dependence upon the ambient humidity and the like because they contain noble metal catalysts as the activators for the responsive material. Thus, they have no practical use as yet.

As to the noxious gas, especially like carbon monoxide, a detecting element having enough sensitivity and high stability for practical use has been required to be developed. However, a highly sensitive and stable detecting element to carbon monoxide has not been put into practice yet. The gas concentration to be detected should be as low as 100 ppm, which is approximately one tenth of that of the other combustible gases like methane, propane or hydrogen.

It is required that detecting elements having great sensitivity to these gases should be remarkably active because of their high chemical stability. Thus, the addition of noble metal catalysts to responsive materials, and the operation of responsive materials at considerably high temperature and the like have been employed to realize a great sensitivity.

Next, the gas sensitive properties of ferric oxide will be described. It was recently found that gamma-type ferric oxide ($\gamma$-$Fe_2O_3$) having a spinel-type crystalline structure has excellent gas detection characteristics. There are various crystalline structures of ferric oxides which are very different from each other in their chemical and physical properties. Among the best known one is alpha-type ferric oxide ($\alpha$-$Fe_2O_3$) having a corundum-type crystalline structure. Besides, $\gamma$-$Fe_2O_3$, $\beta$-$Fe_2O_3$, $\delta$-$Fe_2O_3$, etc. are known. Among them, only the $\gamma$-$Fe_2O_3$ has actually useful gas detection characteristics.

Although $\gamma$-$Fe_2O_3$ has a large sensitivity to hydrogen, ethane, propane and iso-butane, its sensitivity to methane is not always sufficient.

Also $\alpha$-$Fe_2O_3$ has a remarkably small sensitivity not only to methane but also to ethane, propane, iso-butane and carbon monoxide, if the sensitive materials are manufactured from the commercial materials. That is to say the conventional ferric oxides by themselves do not have a sufficiently large sensitivity to combustible gases.

However we found a large sensitivity to combustible gases such as methane in $\alpha$-$Fe_2O_3$ composed of amorphous phase. In spite of its large sensitivity, the amorphous phase $\alpha$-$Fe_2O_3$ does not have sufficient stability and durability in life characteristics because of the degradation caused by crystallization of the amorphous phase, and also is insensitive to carbon monoxide.

Furthermore, by conventional wet processes of hydrolysis and precipitation for preparation of $\alpha$-$Fe_2O_3$, nonuniformity of the precipitated crystalline particle size and congelation of the particles are unavoidable, because of microscopic non-uniformity of the precipitant concentration in the solution. Consequently these cause instability in life characteristics and short durability.

SUMMARY OF THE INVENTION

An object of the present invention is to provide a gas detecting element which has sufficiently high sensitivity to various combustible gases such as methane, ethane, propane and carbon monoxide, high stability and long-time durability, at comparatively low operating temperature without adding noble metal catalyst.

Another object of the present invention is to provide a combustible gas detecting element comprising a crystallized $\alpha$-$Fe_2O_3$ sintered body or film containing sulfate ion, having large sensitivity to combustible gases.

Still another object of the present invention is to realize a great enhancement of the sensitivity in the above $\alpha$-$Fe_2O_3$ and longer durability by adding quadrivalent metal of tin (Sn), zirconium (Zr) or titanium (Ti).

A further object of the present invention is to provide a novel preparation process of the gas sensitive $\alpha$-$Fe_2O_3$ by introducing urea as a precipitant in the wet process, by which extremely uniform microstructure in the $\alpha$-$Fe_2O_3$ can be realized and consequently a high stability in life characteristics and long-time durability can be provided.

A still further object of the present invention is to provide a carbon monoxide (CO) detecting element which can detect CO even in the range of gas concentration as low as 100 ppm, by only adding cadmium (Cd) and/or gold (Au) to the $\alpha$-Fe$_2$O$_3$ sintered body or film containing Sn, Zr or Ti.

The $\alpha$-Fe$_2$O$_3$ gas detecting element according to the present invention can be applied to a highly sensitive and stable combustible gas sensor having an extremely long-time durability in the substantial gas-security market.

The above and other objects, features and advantages will be apparent from consideration of the following description taken in connection with the accompanying drawings.

BRIEF DESCRIPTION OF THE DRAWINGS

FIGS. 4 and 5 are graphs for showing effects of urea used as a precipitant on the change in resistance by long-time operation.

DESCRIPTION OF THE PREFERRED EMBODIMENTS

Figure 1:
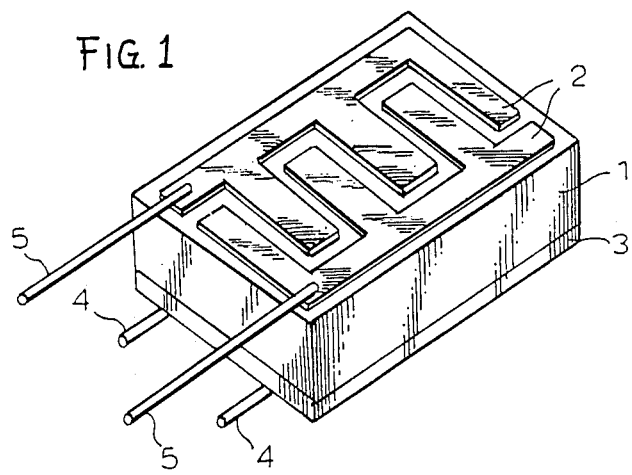
FIG. 1 is a perspective view of an embodiment of a gas detecting element of this invention in the form of a sintered body.
Figure 2:
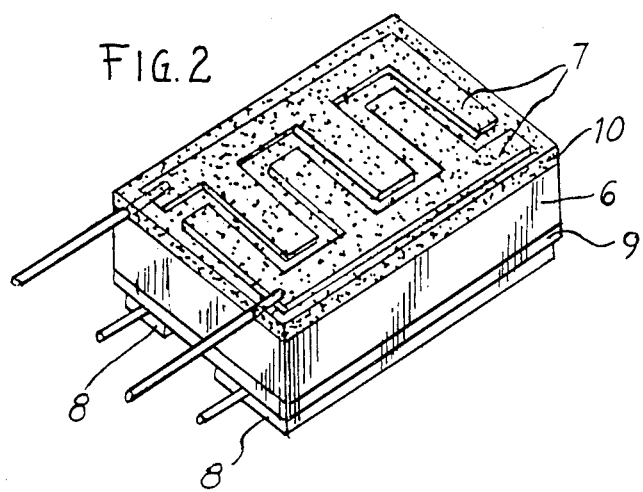
FIG. 2 is a perspective view of an embodiment of a gas detecting element of this invention in the form of a sintered film.

Hereinafter, the preferred embodiments of the present invention will be described in detail in Examples together with the accompanying drawings.

Example 1

To the commercial alpha-ferric oxide ($\alpha$-Fe$_2$O$_3$) reagent was added powdered ferrous sulfate [iron (II) sulfate (Fe$_2$SO$_4$.7H$_2$O)] as a sulfate ion donor at various addition levels, and each of the mixtures was granulated with an organic binder to produce several samples having a particle diameter of 100 to 200 microns. Each of these particulate samples with different ferrous sulfate contents was molded into a rectangular parallelpiped form and sintered in the air at a temperature of 600 degrees C. to obtain a sintered body 1 which is a gas sensitive element. Then, Au was deposited by vacuum vapor deposition on the surface of this sintered body 1 to form a pair of comb-type electrodes 2, while a platinum heating element 3 was affixed to the reverse side with an inorganic adhesive to provide a gas detecting element. An electric current was passed to this heater element through an electrode 4 and the current value was adjusted to control the operating temperature of the gas sensitive element. With the element temperature maintained at 400° C., the change in resistance between electrodes 5 was examined to determine the gas sensitive properties of the gas sensitive element.

Figure 3:
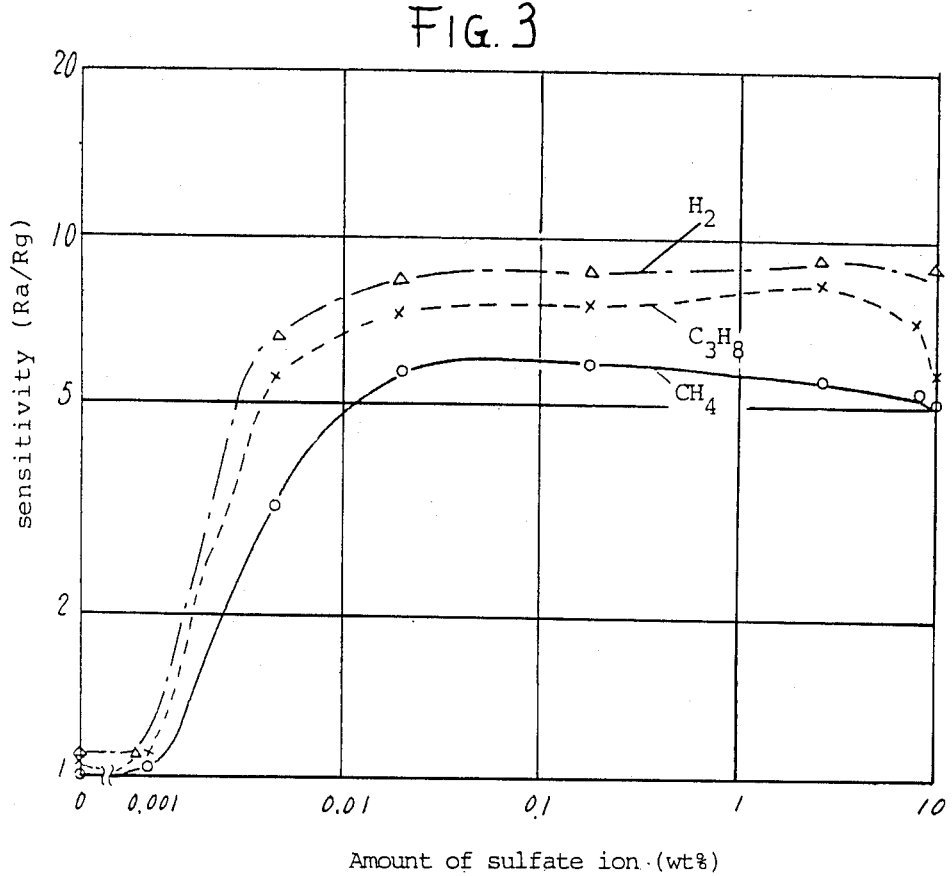
FIG. 3 is a graph for showing the relationship between the amount of sulfate ion and sensitivity.

The resistance value in the air (Ra) was determined in a 50-liter cell in which dry air was gently stirred, while the resistance value in gas (Rg) was determined by introducing into the above cell a gas of at least 99% purity, i.e. methane (CH$_4$), propane (C$_3$H$_8$), isobutane (i-C$_4$H$_{10}$) or hydrogen (H$_2$) at the rate of 10 ppm/sec. each (volume ratio) and measuring the resistance when the concentration of the gas had reached 0.2 volume percent. This particular concentration of 0.2 vol.% was selected because the detectable concentration required of a practical gas detecting element lies somewhere between one to several tenths and a few fractions of the lower explosion limit (LEL) of the gas, and the LEL values of the above-mentioned gases lie somewhere between about 2 volume percent and about 5 volume percent. The presence of sulfate ions (SO$_4^{--}$) in the gas-sensitive element was confirmed by infrared absorption spectrometry and its content was determined by reference to the TG-DTA curve and by fluorescent X-ray spectroscopy. Table 1 shows the response characteristics, in terms of Ra and Rg, of gas-sensitive elements containing different amounts of sulfate ion, and FIG. 3 shows the sensitivity values (Ra/Rg). Incidentally, the value for isobutane is omitted from FIG. 3 because the measured characteristic was similar to that for hydrogen.

It will be apparent from Table 1 and FIG. 3 that the gas responsive characteristic of the element is remarkably improved by the addition of 0.005 to 10.0 weight percent of sulfate ion (SO$_4^{--}$). The limitation of sulfate ion content to the range of 0.005 to 10.0 weight percent in this embodiment was imposed in view of the fact that, as seen from Table 1, the gas-responsive characteristic is not improved at the level of addition below 0.005 weight percent while the presence of more than 10.0 weight percent of sulfate ion interferes with the stability of the characteristics and the mechanical strength of the element. The samples denoted by an asterisk in Table 1 correspond to these cases and are referred to as comparison examples. As represented by No. 1 in the table, the ordinary alpha-Fe$_2$O$_3$ offers only a very small gas-sensitive characteristic value and as such is not practically useful. However, the addition, of sulfate ion thereto results in the development of marked sensitivity to various combustible gases such as methane, etc.

It is generally believed that a metal oxide in more or less amorphous state is more active than in crystalline state as far as physicochemical properties, such as the adsorption and desorption of combustible gases, are concerned. However, even the commercial alpha-Fe$_2$O$_3$ reagent used in this example, which is substantially crystalline, acquires very high activity on addition of sulfate ion, thus displaying a remarkably high gas-sensitive characteristic.

While a sintered body was described in the above example, the fact that the gas-sensitive element need not be a sintered body but may be otherwise will be explained and demonstrated in the following example.

Example 2

In addition to the commercial magnetite (Fe$_3$O$_4$) reagent, there were prepared aqueous solutions containing iron (II) sulfate (FeSO$_4$.7H$_2$O) as a sulfate ion donor in various concentrations. Then, 10 g portions of the above Fe$_3$O$_4$ reagent were weighed and the above aqueous solutions of iron (II) sulfate were added dropwise to these portions, respectively. The resulting mixed powders were heat-treated in vacuum at a temperature of 400° C. Each of the particulate samples were granulated to a particle size of 50 to 100 microns and made into a paste with polyethyleneglycol. On the other hand, as the substrates 6 for the gas detecting elements, alumina substrates 6.5 mm by 5 mm and 0.5 mm thick were prepared and the surface of each substrate was printed with an Au paste in interdigital pattern at a spacing of 0.5 mm and heat-treated to give a pair of comb-type electrodes 7. On the reverse side of the alumina substrate, a commercially available grazed ruthenium oxide heater was printed and heat-treated to provide a heater 9, and then a pair of Au lines were deposited by vacuum vapor deposition to give electrodes 8 for supplying electric power to heater 9.

Then, the above paste was printed on the surface of the substrate in a thickness of about 70 microns, and after allowing to dry at room temperature, the substrate was heated gradually to a temperature of 400° C. and maintained at this temperature for 1 hour. By this stage, the paste is evaporated and the $Fe_3O_4$ oxidized to give a sintered film of gamma-$Fe_2O_3$. The film was further heat-treated at a temperature of 600° C. for 1 hour to cause a transformation of gamma-$Fe_2O_3$ to alpha-$Fe_2O_3$, whereby a sintered film 10 of alpha-$Fe_2O_3$ containing sulfate ions was obtained. The final thickness of the sintered film was about 60 microns.

The sulfate ion content of the gas-sensitive film was determined as follows. A portion of each of the above pastes, instead of being printed on an alumina substrate, was directly heated gradually to a temperature of 400° C. in the same manner as above and TG-DTA and fluorescent X-ray spectroscopy were carried out. The determination of sulfate ions was made by infrared absorption spectroscopy as in Example 1.

The gas-sensitive characteristics of the gas sensitive elements produced as above were determined in the same manner as Example 1. The results are set forth in Table 2. As in Table 1, the asterisked samples are comparison examples.

As explained above, alpha-$Fe_2O_3$ has been thought to be scarcely sensitive to combustible gases (refer to No. 1 in Tables 1 and 2). But alpha-$Fe_2O_3$ can be rendered highly sensitive to the gases by the addition of 0.005 to 10.0 weight percent of sulfate ion thereto. Further, as explained in Examples 1 and 2, a high sensitivity can be obtained by an extremely simple method, i.e. merely adding iron sulfate.

Although iron (II) sulfate as a sulfate ion donor is used in the foregoing Examples 1 and 2, any other materials containing sulfate ion can also be used.

In Examples 1 and 2, the commercial $Fe_2O_3$ and $Fe_3O_4$ reagents were used as starting materials, and iron (II) sulfate was used as a sulfate ion donor. On the other hand, it is known that an alpha-$Fe_2O_3$ sintered body or film containing sulfate ion can also be obtained by heat-treating the powder obtained from an iron salt containing sulfate ion by hydrolysis and precipitation.

Since the gas sensitive element should be heated with a minimum of electric power, the element is also generally constructed as small as possible. Therefore, the uniformity of the composition and microstructure of the element becomes an important factor. The lack of uniformity may result in a variation in characteristics among the elements, an instability in long-time life characteristics of the element and a low reliability thereof. As a means of making the composition and microstructure of the element more uniform, alpha-$Fe_2O_3$ is prepared from the above-mentioned iron salt by the wet process. However, when a precipitant is added to the solution, even if the precipitant is used in a low concentration and the solution is stirred for a long time, the concentration distribution of the precipitant becomes irregular, the formation of crystal nuclei is promoted, the variation in size of precipitated particles is increased, or coagulation occurs. Consequently these phenomena may result in a scatter in characteristics among the elements and an instability in long-time characteristics thereof.

The manufacturing method according to this invention was established after an extensive study of various kinds of precipitants and a series of fabrication processes. The method comprises adding urea [$(NH_2)_2CO$] to an aqueous solution containing iron ion and, as an anion, at least sulfate ion and heating the solution to cause a slow hydrolysis of urea and a consequent gradual increase of pH, thus enabling one to obtain uniform particles.

Hereinafter, the effects brought about by this invention will be explained in detail with reference to comparison examples.

Example 3

80 g of a commercial iron (III) chloride ($FeCl_3.6H_2O$) and 40 g of ammonium sulfate [$(NH_4)_2SO_4$] were dissolved in 1 liter of water, and the solution was stirred at a constant temperature of 80° C. With the temperature maintained at 80° C., 8N-ammonium hydroxide ($NH_4OH$) was added dropwise to the solution at a rate of 60 cc/min. until the pH of the solution reached a value of 7. After completion of the addition, the solution was maintained at a temperature of 60° C. and the precipitate was suction-filtered. The powdery sample thus obtained was dried in a vacuum oven. The dried sample was milled in an agate mortar for two hours, after which it was granulated with an organic binder to prepare particles each having a diameter of 100 to 200 microns. This granulated powder was pressed and sintered in the same manner as in Example 1 to produce a gas sensitive element. This element is represented for convenience as Sample A.

In the case of Sample A, starting materials included both chloride ion and sulfate ion. Next, a sample including only sulfate ion as an anion in the starting material will be explained.

96 g of a commercial iron (III) ammonium sulfate [$Fe_2(SO_4)_3(NH_4)_2SO_4.24H_2O$] was dissolved in 1 liter of water. Thereafter, the same method as used for Sample A was employed to produce a gas sensitive element. This element is represented as Sample B.

Both Samples A and B were prepared by employing $NH_4OH$ as a precipitant. In the preparation of the following two Samples, urea [$(NH_2)_2CO$] instead of $NH_4OH$ was used as a precipitant.

Sample C: 80 g of commercial iron (III) chloride [$FeCl_3.6H_2O$], 40 g of ammonium sulfate [$(NH_4)_2SO_4$] and 60 g of urea [$(NH_2)_2CO$] were dissolved in 1 liter of water and the solution was stirred with heating over a hot plate. The heating was effected for 3 hours at a temperature of 90° C. The pH at the time was 7.0. Thereafter, the same method as used for Samples A and B was employed to produce a gas sensitive element.

Sample D: 96 g of commercial iron (III) ammonium sulfate [$Fe_2(SO_4)_3(NH_4)_2SO_4.24H_2O$] and 60 g of urea [$(NH_2)_2CO$] were dissolved in 1 liter of water and the solution was stirred with heating over a hot plate. Thereafter, the same method as used for Sample C was employed to produce a gas sensitive element.

As aforementioned, in order to examine the effect of using urea as a precipitant, four Samples A through D were prepared. In order to examine scatters in the characteristics of Samples, 50 elements were prepared from each Sample.

Gas sensitive properties were evaluated in the same way as in Example 1. In table 3, Ra of each Sample and the sensitivity and standard deviation of each Sample with relation to 0.5 volume percent of methane, hydrogen and ethanol are shown. It is apparent from Table 3 that the average values of Ra and sensitivity of the Samples C and D using urea as a precipitant are almost the same as those of Samples A and B, but the standard deviation i.e., scatter in characteristics thereof, is extremely small.

Next, the durability characteristics of elements were examined. Samples A through D were compared to one another under two conditions. In one case (a), the elements were operated at a standard operating temperature. In the other case (b), the elements were maintained under a thermally accelerated condition i.e., at a temperature of 600° C. which is much higher than the standard operating temperature of 400° C. (However, the measurement of gas sensitive properties was done at a temperature of 400° C.). It should be noted that methane and hydrogen were used as the test gases. The evaluation of the characteristics variation was performed by examining resistance changes from an initial value. The results of (a) and (b) are shown in FIGS. 4 and 5, respectively. In both cases, with regard to methane, the changing rate of resistance $\Delta R/R$ increases in a positive direction, while with regard to $H_2$ the rate increases in a negative direction. However, it can be understood that the rates of Samples C and D are extremely small compared to those of Samples A and B.

As explained in detail in the foregoing, the production method according to this invention utilizes the precipitation reaction involving hydrolysis of urea in the preparation of material powders for gas sensitive elements. The shape and diameter of each of the obtained powders are considerably uniform. This makes a scatter in gas sensing properties among the gas sensitive elements considerably small and permits production of a gas detecting element which is capable of retaining extremely stable characteristics for a long operating time at a high temperature. Thus, a highly reliable combustible gas detecting element is provided, contributing much to gas security technology.

Now, the effects of additives on sensitive properties of the $\alpha$-$Fe_2O_3$ sintered body or film containing sulfate ions will be described.

First, the sensitivity enhancing effects of the quadrivalent metals, namely Sn, Zn and Ti, will be described by way of the following two examples.

Example 4

To 200 g of a commercial iron (II) oxide ($Fe_2O_3$) [X-ray diffraction analysis showed that it was thoroughly in the $\alpha$-$Fe_2O_3$ phase] was added 40 g of iron (II) sulfate ($FeSO_4 \cdot 7H_2O$) for introduction of sulfate ions, and the mixture was thoroughly milled in an agate mortar. This mixture was divided into several aliquots, and commercial tin (IV) oxide ($SnO_2$), zirconium oxide ($ZrO_2$) or/and titanium oxide ($TiO_2$) were added either alone or in various combinations. Each of the resulting powders was further dry-blended in the agate mortar for 3 hours. To this mixture was added an organic binder, followed by granulation to the size of 100 to 200 microns. Then, in the same manner as Example 1, several samples containing $SnO_2$, $ZrO_2$ or $TiO_2$ in different amounts or/and combinations were prepared.

The presence of sulfate ion ($SO_4^{--}$) in the gas sensitive elements was confirmed by infrared absorption spectroscopy and its contents were assayed by means of the TG-DTA curve and fluorescent X-ray spectroscopy. It was found that these sintered elements contained 0.45 to 0.58 weight percent of sulfate ions.

Figure 6:
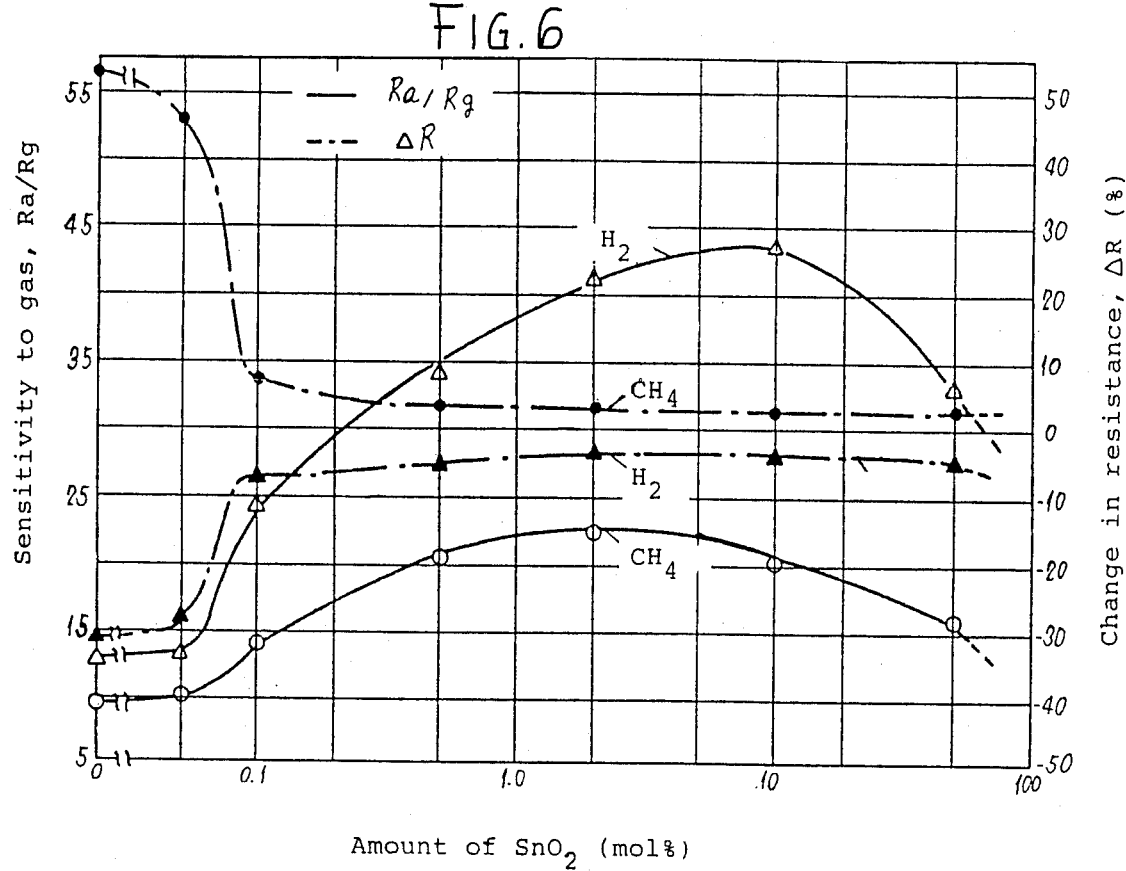
FIGS. 6, 7 and 8 are graphs for showing the dependence of the amount of SnO$_2$, ZrO$_2$ and TiO$_2$ on the gas sensitive properties, respectively.
Figure 7:
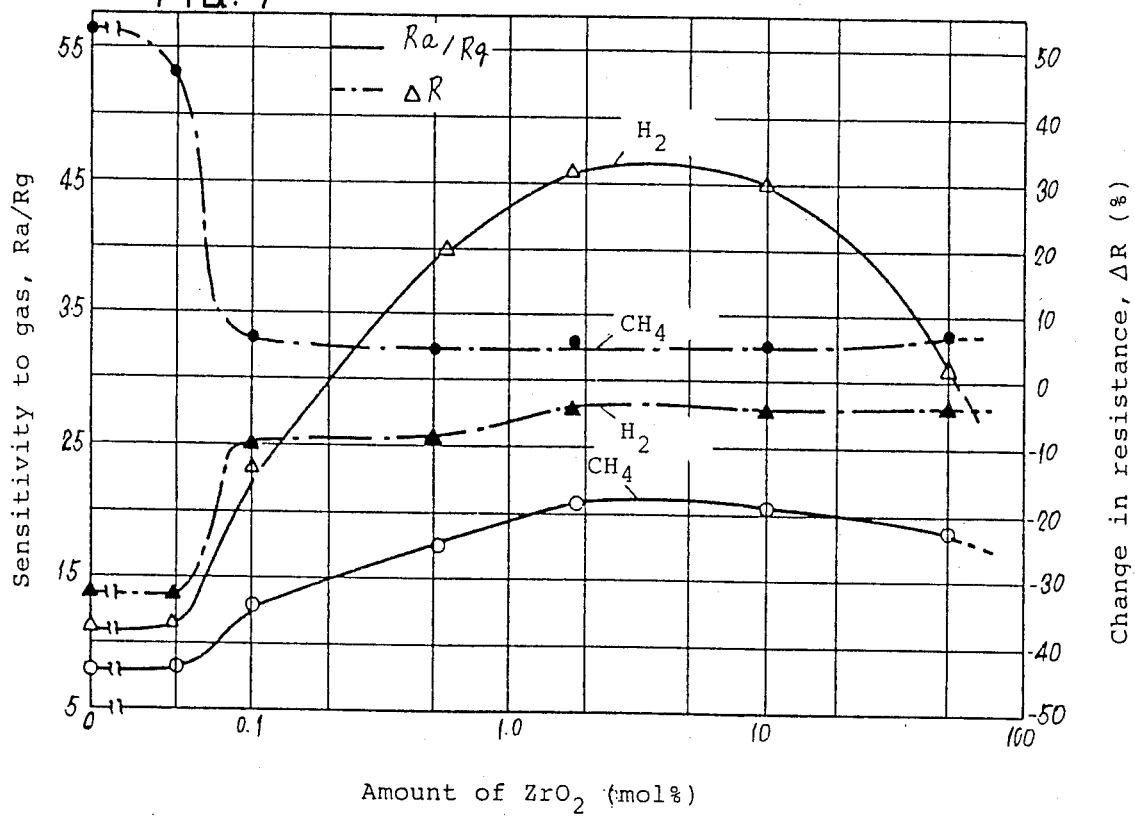
Figure 8:
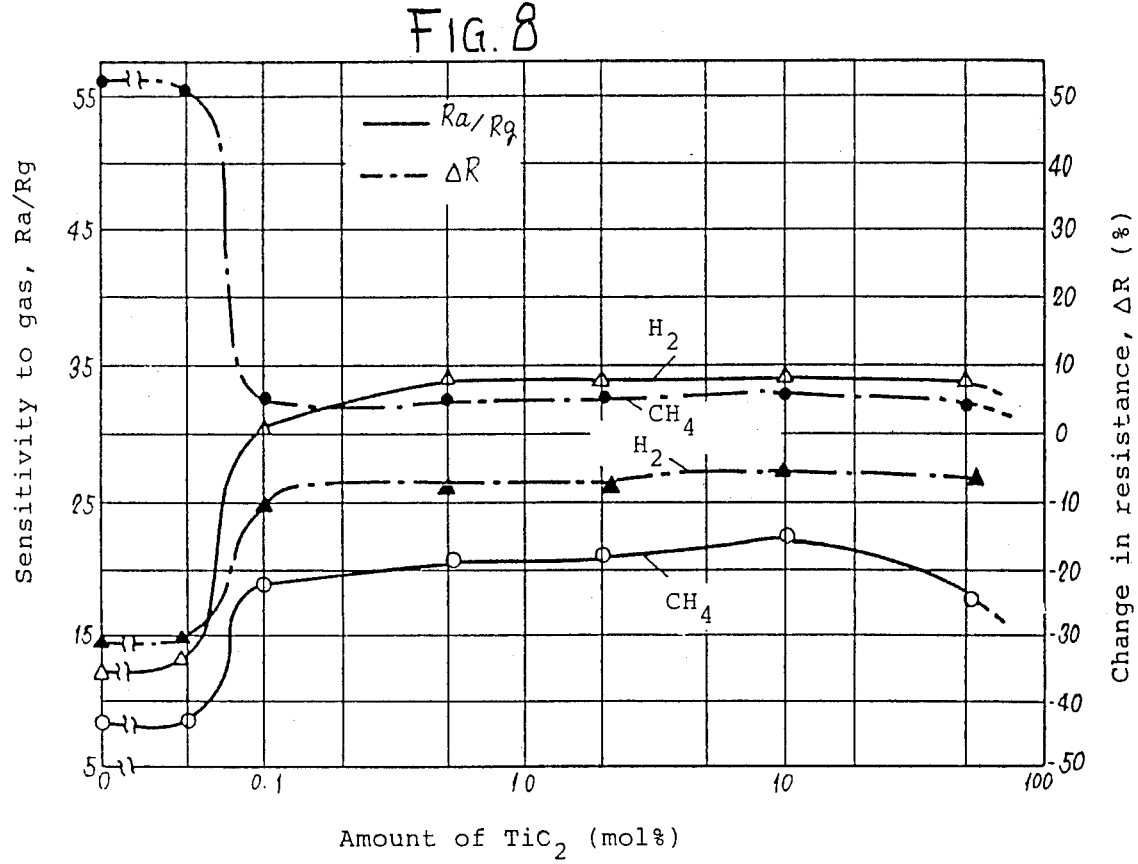

FIGS. 6 through 8 show the addition level dependency of gas sensitive properties in the cases of single addition of said additives. The gas sensitive characteristic was evaluated in terms of (i) gas sensitivity (Ra/Rg) and (ii) change in resistance vs. operating time ($\Delta R$) (the percent change relative to the initial value in the resistance of the element after operating at 400° C. for 2000 hours).

It will be apparent from FIGS. 6 through 8 and Table 4 that the addition of Sn, Zr or/and Ti either independently or in combination caused remarkable improvements in gas sensitive properties (gas sensitivity: Ra/Rg). What is further noteworthy is the reduced change in resistance vs. operating time. Here, the change was drastically decreased by the addition of said additives. Thus, the addition of Sn, Zr or Ti leads to the very remarkable enhancement of gas sensitive properties and reliability.

The total amount of additives in the present invention is limited to the range of 0.1 to 50 mole percent based on the total composition of the sintered element, and is predicated on the following considerations. Thus, as will be seen from FIGS. 6 through 8 and Table 4, the addition level of less than 0.1 mole percent is not conducive to the desired degrees of improvement in gas sensitive properties and reliability, while an excess of additives over 50 mole percent increases the very resistance of the element and interferes with the stability of its characteristics. The samples marked with an asterisk in the table correspond to such cases, which are referred to in Table 4 as comparison samples.

Now, it is generally acknowledged that compared with a crystalline metal oxide, the metal oxide partially in amorphous state is liable to be more active in physiochemical reactions such as adsorption phenomenon. However, even the substantially 100% crystallized commercial $\alpha$-$Fe_2O_3$ as used in this example displays very high activity on incorporation of sulfate ions and addition of Sn, Zr or Ti. Moreover, since this activity remains stable without aging effects, the element made thereof affords an extremely high gas sensitivity and a high reliability as a consequence.

In Example 4, the cases in which the amount of sulfate ion was unvaried but additives were varied in amount or/and combination were described. In Example 5 which follows, the kind and level of addition of such additives were held constant but the amount of sulfate ion was varied. Thus, in Example 5, it is confirmed that this invention is still valid even when the gas sensitive element is in the form of a sintered film and the influence of the amount of sulfate ion on gas sensitive properties will be described.

Example 5

To 100 g of commercial ferric oxide were added commercial tin(IV) oxide ($SnO_2$), zirconium oxide ($ZrO_2$) and titanium oxide ($TiO_2$) in the varying proportions indicated in Table 5. Such mixtures were evenly blended in an agate morotar. Each of the resulting powdery mixtures was divided into 8 aliquots, and solutions of iron (II) sulfate ($FeSO_4 \cdot 7H_2O$) prepared in various concentrations were added. Then, the powders were mixed well in the mortar for 1 hour. As typical samples, 3 samples containing different oxides (samples A to C) and 8 samples containing different amounts of sulfate ion for each oxide composition or a total of 24 samples were obtained.

Figure 9:
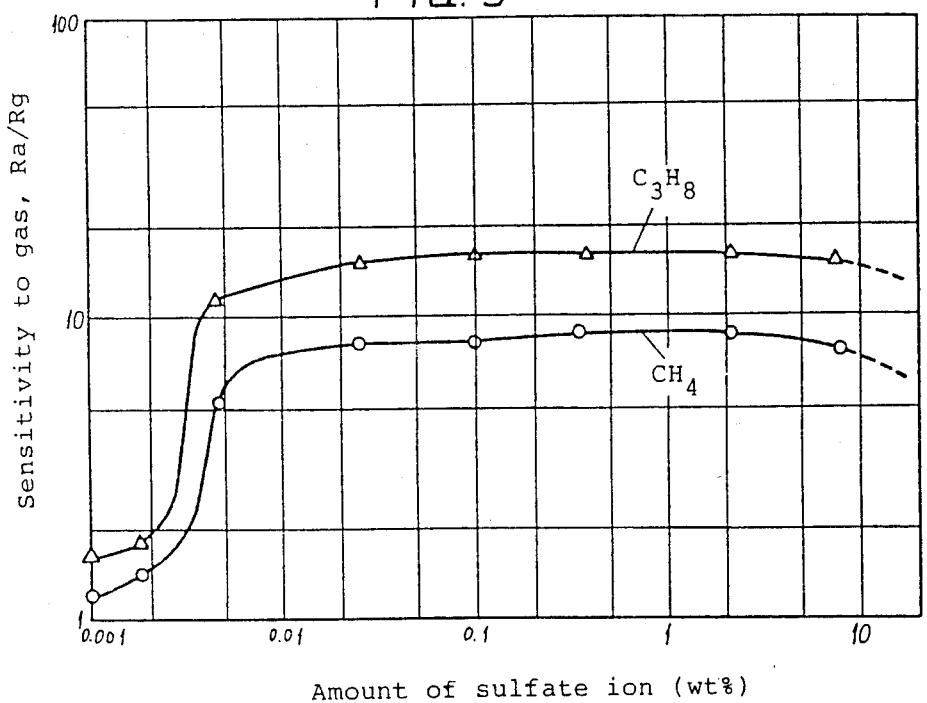
FIGS. 9, 10 and 11 are graphs for showing the effects of sulfate ion on enhancement of sensitivity.
Figure 10:
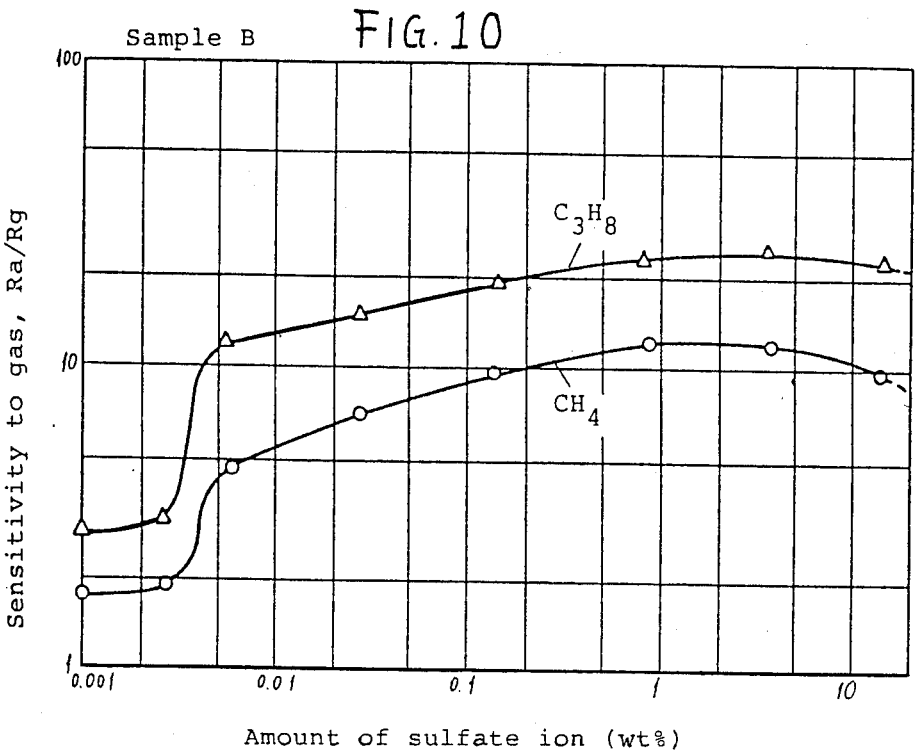
Figure 11:
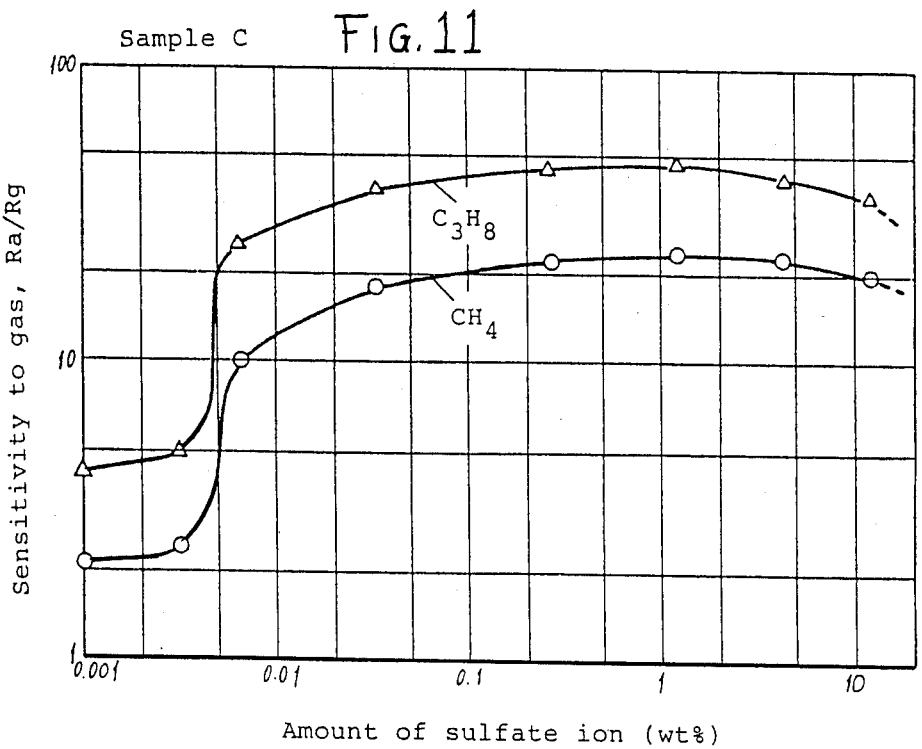

These mixed powders were calcined in the air at 400° C. for 2 hours, after whih they were granulated to the particle size of 50 to 100 microns. Thereafter following the procedure described in Example 2, gas sensitive elements were prepared and their gas sensitive properties were measured. FIGS. 9 through 11 show the correlation of the gas sensitivity (Ra/Rg) and sulfate ion level of Samples A to C, respectively. Table 6 shows the changes in resistance vs. operating time of Samples A–C at a typical sulfate ion level of 2 to 5 weight percent. It should be understood that in this example methane and propane were used as test gases.

It will be apparent from FIGS. 9 through 11 that even when the gas sensitive element is a sintered film, substantially the same characteristics as those found in Example 4 can be obtained. Moreover, it is apparent if only from Table 4 that the change in resistance vs. operating time is very small as was true in Example 4.

As will be apparent from FIGS. 9 through 11, the effect of addition of Sn, Zr or Ti is not observed when the amount of sulfate ion is less than 0.005 weight percent, thus failing to accomplish the object of this invention. Conversely, if the sulfate ion level is over 10.0 weight percent, the product will be deficient in practical utility, namely in the stability of characteristics or in mechanical strength. It is for the above reasons that the amount of sulfate ion to be contained in the gas sensitive element of this invention is limited to the range of 0.005 to 10.0 weight percent.

Now, while commercial oxide reagents were used as starting materials in Examples 4 and 5, this invention is only delimited by the above range of final gas sensitive element composition and should not be considered to be restricted in any manner by any specific starting materials and production processes. Moreover, while methane and hydrogen or propane were used as test gases in the foregoing examples, the effects of the invention are not limited to these particular gases. Rather, it is obvious that the invention is also effective for ethane, isobutane, ethanol and other combustible gases.

The gas sensitive elements described in Examples 4 and 5 are either sintered bodies or sintered films each based on $\alpha$-$Fe_2O_3$ and containing sulfate ions and Sn, Zr or/and Ti, and the incorporation of sulfate ion and the addition of said additive metals result in a remarkable enhancement of gas sensitivity. Thus, even in the case of methane gas, the detection of which in trace amounts could hardly be accomplished without the employment of a noble metal catalyst, a very high sensitivity can now be realized even at a comparatively low temperature of 400° C. Another effect that can be obtained by the use of such additives is a remarkable life prolongation effect, i.e. a drastic reduction of change in resistance vs. operating time. In other words, this means a great contribution to the enhancement of reliability which is the most important factor in gas detecting elements for practical use.

As stated hereinbefore, these additives enhance the sensitivity of elements a great deal in relation to hydrocarbon gases such as methane, propane, isobutane, etc., hydrogen, alcohol and other combustible gases. However, the additives have very little effects with respect to carbon monoxide (CO).

Therefore, in order to increase the sensitivity of the element to carbon monoxide, various other additives were investigated. As a result, it was found that cadmium (Cd) and gold (Au) increase the sensitivity of the element to carbon monoxide without interferring with its other gas sensitive properties. Thus, by adding Cd and/or Au further to the $\alpha$-$Fe_2O_3$ sintered body containing sulfate ion and, as added thereto, Sn, Zn or/and Ti, there can be obtained a gas sensitive element having a practically useful sensitivity even to carbon monoxide present in the concentration order of as low as 100 ppm.

In Example 6 that follows, the effect of addition of Cd and Au will be explained in detail.

Example 6

To 3 liters of water were added 90 g of commercial iron(III) chloride ($FeCl_3.6H_2O$) and 180 g of iron(II) sulfate ($FeSO_4.7H_2O$), and the mixture was stirred at a temperature of 50° C. for 10 minutes. To this solution were added 5 mole % each of Sn (IV) chloride ($SnCl_4.5H_2O$) solution, zirconium oxychloride ($ZrOCl_2.8H_2O$) solution and titanium (IV) sulfate $Ti(SO_4)_2$ solution, and the mixture was further stirred at the same temperature of 50° C. for 10 minutes. With stirring, 8-N ammonium hydroxide was added dropwise at the rate of 60 cc/min. until the pH of the solution became pH 7. The resulting precipitate was collected by filtration and dried in the air at 110° C. for 20 hours. This dry powder was crushed in an agate mortar for 1 hour.

This powder was divided into 12 aliquots. Then, commercial cadmium oxide (CdO) and chloroauric acid ($HAuCl_4.4H_2O$) were respectively dissolved in water to prepare solutions of 100 mg/ml concentration. These solutions were added to the above-mentioned aliquots at the addition levels indicated in Table 7, and each mixture was milled in an agate mortar. Using these 12 powders, the procedure of Example 1 was repeated to prepare sintered elements. In this example, however, the sintering temperature and the operating temperature were 500° C. and 350° C., respectively. As the test gases, carbon monoxide (CO), methane ($CH_4$), propane ($C_3H_8$) and hydrogen ($H_2$) were employed. The allowable concentration of CO for human health is generally acknowledged to be 100 ppm. Therefore, the evaluation of gas sensitivity was made at the concentration level of 100 ppm for all the gases mentioned so that a definite direct comparison could be made among them.

The test results are set forth in Table 7. It is clear that the addition of at last one of Cd and Au in the amounts of 1.0 to 20 weight % as CdO and 0.1 to 10 weight % as Au results in a remarkable increase in sensitivity to CO. This effect is not seen when the level of addition is below the above-mentioned range. On the other hand, when the level exceeds the range, the characteristics of the elementbecome so unstable that it cannot be of practical value. Such samples are indicated by the asterisk mark in Table 7. It is for the foregoing reason that the amounts of Cd and Au are defined as above.

This Example pertains to cases in which all of the metals in the first additive group, namely Sn, Zr and Ti, are contained in the compositions but the above-described effect of addition of Cd and/or Au is not limited to such cases but is realized in cases where at least one of Sn, Zr and Ti is contained. This will be demonstrated using several typical samples prepared in the same manner as Example 6. In these cases, the amounts of Cd and Au were held constant. The results are shown in Table 8.

It will be seen from Table 8 that the addition of Cd and Au is not only useful in the co-presence of all of the first group additives, i.e. Sn, Zr and Ti, but also provides beneficial effects when at least one of these metals Sn, Zr and Ti is co-present in the composition.

It will also be apparent from the set of experiments described in Example 6 that the co-presence of at least one of the first group additives (Sn, Zr, Ti) and at least one of the second group additives (Cd, Au) in a sulfate ion-containing $\alpha$-$Fe_2O_3$ sintered body results in a remarkably high sensitivity even to a very low concentration of CO in the order of 100 ppm.

To detect a low concentration of CO with high sensitivity, it was common practice to employ a noble metal catalyst such as Pd and Pt. In accordance with this invention, a very high sensitivity even to a low concentration of CO can be realized by the mere addition of Cd and/or Au as described above. This invention thus not only provides a very beneficial gas detecting element capable of preventing health hazards due to carbon monoxide poisoning but also provides a sensor for combustion control. In fact, a broad range of application possibilities is expected.

In Examples 1 through 6, the gas sensitive element of this invention was constructed in the form of a sintered body or a sintered film, both as produced by sintering in the atmospheric air. However, this invention is not specifically limited by sintering conditions such as sintering temperature, time and atmosphere but rather any sintering conditions can be employed only if products are made available in the form of sintered bodies or films. Further, any description or statement in this specification should by no means be construed as precluding addition of additives which may be termed third group additives.

Moreover, while Example 3 sets forth the effect of using area as a precipitant for the preparation of raw materials for the gas sensitive element, this effect of urea is manifested not only in the absence of additives as in Example 3 but also in the presence of additives such as Sn, Zr and Ti and/or Cd and Au.

TABLE 1

| No. | Content of sulfate ion (wt %) | Resistance in clean air Ra (kΩ) | Resistance in air containing 0.2 vol % of gas Rg (kΩ) | | | |
|---|---|---|---|---|---|---|
| | | | $CH_4$ | $C_3H_8$ | $i$-$C_4H_{10}$ | $H_2$ |
| *(1) | 0 | 430 | 427 | 403 | 392 | 397 |
| *(2) | 0.001 | 442 | 430 | 408 | 398 | 399 |
| (3) | 0.005 | 609 | 191 | 100 | 82 | 86 |
| (4) | 0.018 | 673 | 117 | 96 | 80 | 81 |
| (5) | 0.16 | 694 | 112 | 95 | 78 | 80 |
| (6) | 2.8 | 743 | 123 | 96 | 79 | 82 |
| (7) | 7.3 | 805 | 139 | 102 | 88 | 90 |
| (8) | 10.0 | 943 | 156 | 113 | 94 | 96 |
| *(9) | 12.6 | 1098 | (unable to measure) | | | |

*Comparison sample

TABLE 2

| No. | Content of sulfate ion (wt %) | Resistance in clean air Ra (kΩ) | Resistance in air containing 0.2 vol % of gas Rg (kΩ) | | | |
|---|---|---|---|---|---|---|
| | | | $CH_4$ | $C_3H_8$ | $i$-$C_4H_{10}$ | $H_2$ |
| *(1) | 0 | 588 | 382 | 67 | 60 | 64 |
| *(2) | 0.001 | 629 | 426 | 72 | 66 | 68 |
| (3) | 0.005 | 733 | 101 | 60 | 54 | 57 |
| (4) | 0.034 | 808 | 94 | 60 | 50 | 55 |
| (5) | 0.17 | 867 | 96 | 66 | 54 | 58 |
| (6) | 1.8 | 1040 | 109 | 71 | 62 | 67 |
| (7) | 6.3 | 1250 | 133 | 90 | 79 | 84 |
| (8) | 10.0 | 1330 | 153 | 106 | 93 | 96 |
| *(9) | 11.8 | 1570 | (unable to measure) | | | |

*Comparison sample

TABLE 3

| Sample | Ra (MΩ) | Sensitivity Ra/Rg (5000 ppm) | | | | | |
|---|---|---|---|---|---|---|---|
| | | $CH_4$ | | $H_2$ | | $C_2H_5OH$ | |
| | | $\overline{X}$ | s | $\overline{X}$ | s | $\overline{X}$ | s |
| A | 2.2 | 2.8 | 0.3 | 8.0 | 1.0 | 6.1 | 0.9 |
| B | 2.8 | 3.2 | 0.3 | 9.3 | 1.2 | 6.5 | 1.0 |
| C | 2.0 | 2.7 | 0.1 | 7.5 | 0.3 | 5.8 | 0.3 |
| D | 2.5 | 2.9 | 0.1 | 8.2 | 0.3 | 6.3 | 0.3 |

$\overline{X}$: Average
S: Standard deviation

TABLE 4

| Additives (mol %) | | | Sensitivity Ra/Rg (ΔR (%)) | |
|---|---|---|---|---|
| $SnO_2$ | $ZrO_2$ | $TiO_2$ | $CH_4$ | $H_2$ |
| 0.02 | 0.02 | 0.02 | 6.9 (+48) | 13* (−41) |
| 0.1 | 0.1 | — | 14 (+7.3) | 36 (−8.1) |
| 0.1 | — | 0.1 | 15 (+6.1) | 40 (−5.8) |
| — | 0.1 | 0.1 | 15 (+5.5) | 39 (−7.2) |
| 1.0 | 1.0 | 1.0 | 21 (+4.0) | 52 (−4.9) |
| 5.0 | 5.0 | 5.0 | 22 (+4.4) | 48 (−3.9) |
| 10 | 10 | 10 | 12 (+4.8) | 28 (−6.6) |
| 20 | 20 | 20 | unable to measure* | |

*Comparison sample

TABLE 5

| Sample | Additives (mol %) | | |
|---|---|---|---|
| | $SnO_2$ | $ZrO_2$ | $TiO_2$ |
| A | 0.2 | 0.2 | 0.2 |
| B | 2.0 | 2.0 | 2.0 |
| C | 10 | 10 | 10 |

TABLE 6

| Sample | Change in Resistance ΔR (%) | |
|---|---|---|
| | $CH_4$ | $C_3H_8$ |
| A | +7.3 | −8.1 |
| B | +6.2 | −5.2 |
| C | +5.0 | −7.3 |

TABLE 7

| Sample | Additive (wt %) | | Sensitivity Ra/Rg (100 ppm) | | | |
|---|---|---|---|---|---|---|
| | CdO | Au | CO | $CH_4$ | $C_3H_8$ | $H_2$ |
| 1 | 0 | 0 | 1.4 | 4.3 | 5.6 | 4.0* |
| 2 | 0.5 | 0.05 | 1.5 | 4.4 | 5.2 | 4.2* |
| 3 | 1.0 | 0.1 | 4.9 | 5.2 | 5.4 | 4.0 |
| 4 | 2.0 | 0 | 5.3 | 5.5 | 6.0 | 4.4 |
| 5 | 0 | 0.2 | 5.0 | 5.4 | 5.7 | 4.0 |
| 6 | 5.0 | 0.5 | 6.0 | 6.2 | 5.6 | 4.2 |
| 7 | 7.0 | 0 | 6.1 | 6.8 | 5.4 | 4.6 |
| 8 | 2.0 | 5.0 | 7.0 | 6.4 | 5.7 | 4.2 |
| 9 | 0 | 2.0 | 5.3 | 5.0 | 5.1 | 4.4 |
| 10 | 10 | 5.0 | 5.2 | 4.8 | 5.6 | 4.0 |
| 11 | 20 | 10 | 4.8 | 4.9 | 5.0 | 4.4 |
| 12 | 25 | 15 | unable to measure* | | | |

*Comparison sample

TABLE 8

| Additives | | | | | Sensitivity | | | |
|---|---|---|---|---|---|---|---|---|
| 1st group (mol %) | | | 2nd group (wt %) | | Ra/Rg (100 ppm) | | | |
| $SnO_2$ | $ZrO_2$ | $TiO_2$ | CdO | Au | CO | $CH_4$ | $C_3H_8$ | $H_2$ |
| 0 | 0 | 0 | 5.0 | 0.5 | 3.2 | 2.1 | 4.0 | 2.2 |
| 10 | 0 | 0 | | | 6.5 | 6.8 | 7.8 | 5.0 |
| 0 | 10 | 0 | | | 5.8 | 6.4 | 6.8 | 4.7 |
| 0 | 0 | 10 | | | 6.4 | 6.9 | 7.1 | 4.0 |
| 5 | 5 | 0 | | | 6.0 | 6.1 | 6.4 | 4.9 |
| 5 | 0 | 5 | | | 5.6 | 5.8 | 6.1 | 4.4 |
| 0 | 5 | 5 | | | 5.9 | 5.8 | 5.7 | 4.4 |
| 5 | 5 | 5 | | | 6.0 | 6.2 | 5.6 | 4.2 |

What is claimed is:

1. A combustible gas detecting element comprising:
   a sintered body of $\alpha$-$Fe_2O_3$ containing 0.005 to 10 weight percent of sulfate ions; and
   a pair of spaced apart electrodes attached to said sintered body of $\alpha$-$Fe_2O_3$ for applying an electric current to said sintered body,
   whereby the presence of a combustible gas may be detected as a change in electrical resistance between said pair of electrodes.

2. A combustible gas detecting element according to claim 1, wherein said sintered body contains 0.018 to 10 weight percent of sulfate ions.

3. A combustible gas detecting element according to claim 1, wherein said sintered body contains 0.16 to 10 weight percent of sulfate ions.

4. A combustible gas detecting element comprising:
   a sintered body of $\alpha$-$Fe_2O_3$ containing 0.005 to 10 weight percent of sulfate ions, and at least one additive selected from the group consisting of the dioxides of tin, zirconium and titanium, the total amount of said at least one additive being 0.1 to 50 mole percent; and
   a pair of spaced apart electrodes attached to said sintered body for applying an electric current to said sintered body,
   whereby the presence of a combustible gas may be detected as a change in electrical resistance between said pair of electrodes.

5. A combustible gas detecting element according to claim 4, wherein said sintered body contains 0.018 to 10 weight pecent of sulfate ions.

6. A combustible gas detecting element according to claim 4, wherein said sintered body contains 0.16 to 10 weight percent of sulfate ions.

7. A combustible gas detecting element according to claim 4, wherein said sintered body further contains at least one further additive selected from the group consisting of cadmium, as CdO, wherein the amount of cadmium, when present, is 1 to 20 weight percent, and the amount of gold, when present, is 0.1 to 10 weight percent.

8. A combustible gas detecting element comprising:
   a supported sintered film of $\alpha$-$Fe_2O_3$ containing 0.005 to 10 weight percent of sulfate ions; and
   a pair of spaced apart electrodes attached to said sintered film of $\alpha$-$Fe_2O_3$ for applying an electric current to said sintered film,
   whereby the presence of a combustible gas may be detected as a change in electrical resistance between said pair of electrodes.

9. A combustible gas detecting element according to claim 8, wherein said sintered film contains 0.018 to 10 weight percent of sulfate ions.

10. A combustible gas detecting element according to claim 8, wherein said sintered film contains 0.16 to 10 weight percent of sulfate ions.

* * * * *